United States Patent [19]

Abrams

[11] Patent Number: 4,867,962
[45] Date of Patent: Sep. 19, 1989

[54] FUNCTIONALLY SPECIFIC ANTIBODIES

[75] Inventor: Paul G. Abrams, Seattle, Wash.

[73] Assignee: NeoRx Corporation, Seattle, Wash.

[21] Appl. No.: 160,648

[22] Filed: Feb. 26, 1988

[51] Int. Cl.⁴ .............................................. A61K 49/02
[52] U.S. Cl. .......................................... 424/1.1; 424/9
[58] Field of Search ................................ 424/1.1, 9, 85

[56] References Cited

U.S. PATENT DOCUMENTS 4,478,815 10/1984 Burchiel et al. ...................... 424/1.1
4,624,846 11/1986 Goldenberg .......................... 424/1.1

Primary Examiner—John S. Maples
Attorney, Agent, or Firm—Seed and Berry

[57] ABSTRACT

Diagnostic or therapeutic agents are attached to two or more antibody species having non-overlapping patterns of cross-reactivity to increase the relative amount of the active agent(s) delivered to desired target cells compared to non-target cells. The agents may be attached to monoclonal antibodies which bind to cancer cells so that a higher percentage of the active agent(s) localize on the target cells compared to each type of cross-reactive normal tissue.

40 Claims, 1 Drawing Sheet

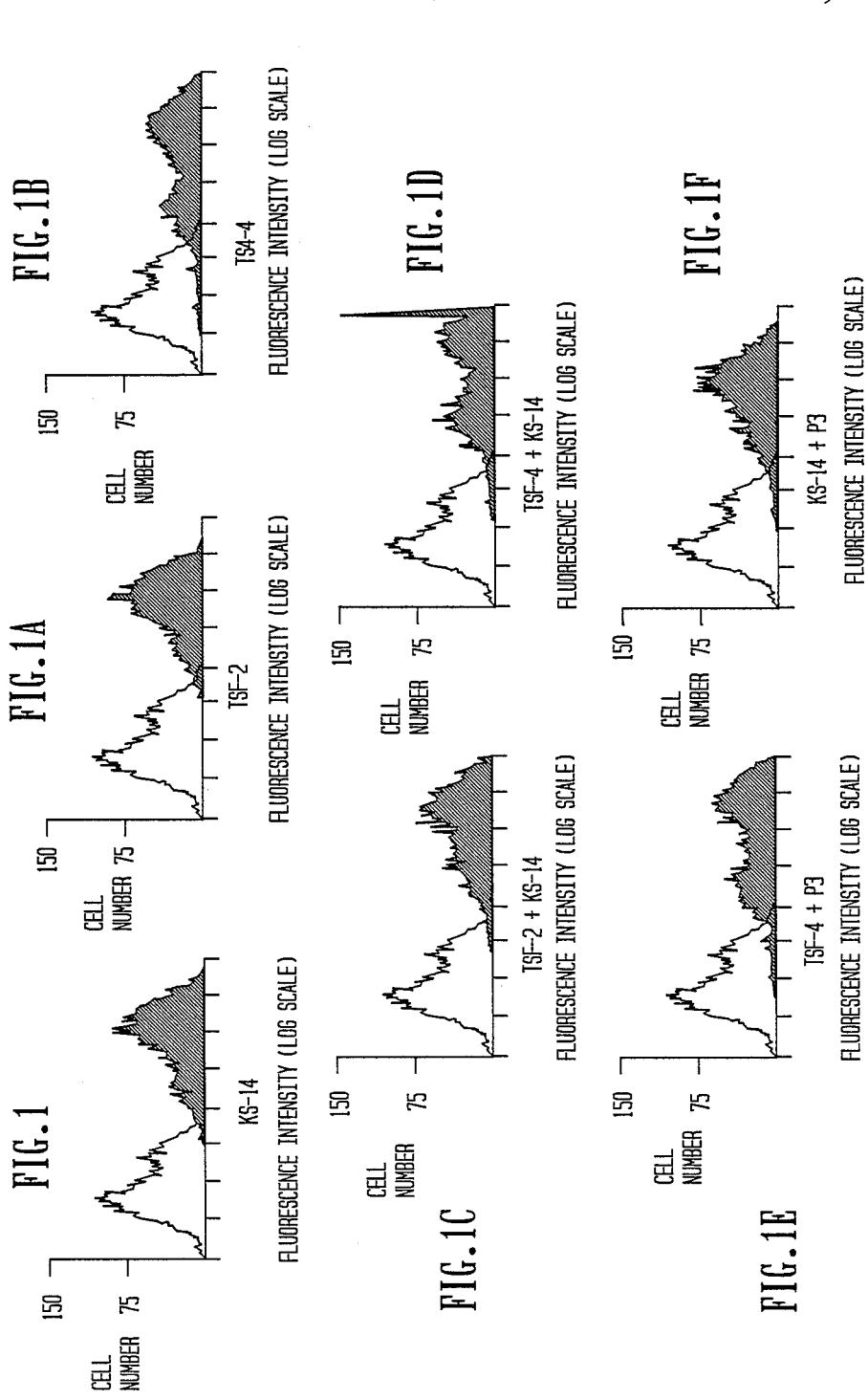

FUNCTIONALLY SPECIFIC ANTIBODIES

TECHNICAL FIELD

The present invention relates to methods for increasing the relative amount of antibody-linked diagnostic or therapeutic agents delivered to target tissues in vivo compared to the amount of such agents delivered to non-target tissues. Methods for enhancing specific delivery of one or more diagnostic or therapeutic agents (bound to tumor-specific monoclonal antibodies) to a cancer site, while reducing the percentage of administered agents which bind to cross-reactive normal tissues, are provided.

BACKGROUND

In 1901, antibodies were described as magic bullets, and it was suggested that their specificity could be employed to direct therapies at a population of cells whose eradication was desirable. The decades since this vision have witnessed repeated attempts to generate antibodies directed against antigens that are absolutely specific for a defined population of cells, such as tumor cells. Monoclonal antibodies have been generated that react with tumor cells to a greater degree than with normal tissues, but none have been shown to be absolutely specific for tumor cells. With the possible exception of the antigens associated with B-cell lymphoma against which anti-idiotype antibodies are directed, no tumor-specific antigens suitable as targets for antibody-guided therapy have been discovered. Instead, antigens with quantitatively augmented expression on tumors and/or restricted and/or diminished expression on normal tissues have been used to develop antibodies for diagnostic and therapeutic uses. When normal cross-reactive tissues are not vital or replicable (e.g., normal T-cells), the problems associated with delivery of diagnostic or therapeutic agents to non-target cross-reactive tissues are less acute. However, the more potent the therapy, the more cross-reactivity may compromise safety and, therefore, the maximum tolerated dose that may be administered is lowered. Delivery of diagnostic agents to normal cross-reactive tissues may result in misdiagnosis.

A need remains for antibodies of improved specificity for target tissue such as tumors and decreased cross-reactivity with non-target (e.g., normal) tissues. This would be accomplished by identification of absolutely tumor-specific antigens and antibodies or by improved immunization techniques to yield totally tumor-specific antibodies. It is possible, however, that such target tumor-specific antigens do not exist, and that antibodies having the desired degree of specificity therefore will never be isolated.

SUMMARY OF THE INVENTION

The present invention provides a method of delivering one or more diagnostic or therapeutic agents to a target site within a mammalian or human host, comprising administering to said host two or more different antibody species, each having one of said agents attached thereto, wherein each of said antibody species is reactive with a different epitope on the target site and wherein the patterns of cross-reactivity for each antibody species are non-overlapping. Each of the antibody species may have a diagnostic agent attached thereto. Alternatively, the antibody species may have the same or different therapeutic agents (e.g., radioisotopes, toxins, or drugs) attached thereto. In one embodiment of the invention, each antibody species is a monoclonal antibody reactive with a cancer cell.

Also provided by the present invention is a method of producing additive accumulation of two or more immunoconjugates on a target tissue within a human or mammalian host while minimizing additive accumulation of the immunoconjugates on non-target tissues, comprising:

a) administering a first immunoconjugate comprising a first antibody species to the host;

(b) administering one or more additional immunoconjugates each comprising a different antibody species to the host, wherein each of the antibody species reacts with a different epitope on the target tissue and the different antibody species have non-overlapping patterns of cross-reactivity.

The present invention also provides a method of administering two or more different therapeutic agents to a human or mammalian host to eradicate target cells, wherein each therapeutic agent is administered at or near its maximum tolerated dose to the host, while minimizing toxicity toward non-target tissue comprising attaching each different therapeutic agent to a different antibody species, wherein each antibody species reacts with a different epitope on the target cells, and wherein the patterns of cross-reactivity for each antibody species are non-overlapping, and administering each of the resulting immunoconjugates at or near the maximum tolerated dosage to the host.

Use of antibody species having non-overlapping cross-reactivity in accordance with the present invention provides advantages which include reduced chances of misdiagnosis (in the case of diagnostic agents) and reduced toxicity toward non-target tissues (in the case of the therapeutic agents).

BRIEF DESCRIPTION OF THE FIGURES

FIG. 1 depicts the binding of three monoclonal antibodies with small cell lung cancer cells, as determined by flow cytometry.

DETAILED DESCRIPTION OF THE INVENTION

The present invention provides methods for delivering diagnostic or therapeutic agents to a desired target site within a human or mammalian host. The agents are attached to two or more different antibody species which are reactive with different epitopes (on the same or different antigens) on the target site but which have non-overlapping patterns of cross-reactivity. An epitope is an antigenic determinant, and a given antigen may comprise more than one epitope. Thus, the different antibodies (along with the agents attached thereto) accumulate additively on the desired target site, while only one antibody species accumulates on each type of cross-reactive non-target tissue. Additive accumulation of two or more of the immunoconjugates on non-target tissues thus is minimized or eliminated. A higher percentage of the administered agent therefore becomes localized in vivo on the target site compared to the non-target tissues. In the case of diagnostic agents, target sites can be more clearly detected or imaged against a comparatively lower "background" of the agent on non-target sites, and the incidence of misdiagnosis may be reduced as a result. For therapeutic agents, the comparatively lower amount of agent delivered to non-target sites results in reduced toxicity toward normal tissues.

As discussed above, antibodies with 100% specificity to a desired target site have yet to be isolated, in spite of the significant effort that has been directed toward that goal. The only possible exceptions are anti-idiotype antibodies, but any such antibody is specific for the B-lymphoma cells of only one individual, and thus must be separately developed and isolated for each new patient. The use of two or more antibodies specific for a target site but with non-overlapping cross-reactivity to normal tissues, in accordance with the present invention, provides a method of increasing the proportionate amount of antibody-bound agent(s) that become localized at a target site compared to non-target sites, even though a single antibody having such increased target specificity has not been isolated.

As used herein, the statement that the patterns of cross-reactivity for each of the antibody species are non-overlapping means that the list of non-target tissues to which one antibody species binds is substantially different from the list of non-target tissues to which the second antibody species binds If a third antibody species is to be administered to the same patient, an antibody is used which has a pattern of cross-reactivity that is substantially different from that of both the first and the second antibody species. The patterns of cross-reactivity are to be different enough to produce the desired results of the method of the invention, namely, proportionately less of the agent on non-target tissues such that background is reduced (in the case of diagnostic agents) and toxicity to normal tissues is reduced (in the case of therapeutic agents). The desired results may still be achieved in some cases when the patterns of cross-reactivity for the different antibody species include a very small number of the same non-target tissues. For example, two antibodies may both cross-react with a non-target cell type (e.g., normal T-cells) which is not essential to the health of the patient, so the desired reduction in toxicity to the patient is achieved in spite of additive accumulation of therapeutic agents bound to these antibodies on the non-essential cell type. However, it is preferable to choose antibody species which do not cross-react with any of the same non-target tissues.

The method of the present invention generally begins with identification of the two or more antibodies to be employed. As discussed above, antibody species which bind to the desired target site but which have negligible or no overlapping cross-reactivity to non-target sites are chosen for use.

The antibody species employed in the present invention may be intact antibody molecules, fragments thereof, or functional equivalents thereof, including genetically engineered variations thereof. Examples of antibody fragments are F(ab')$_2$, Fab', Fab, and Fv, produced by conventional procedures. While polyclonal antibodies may be employed in the present invention, monoclonal antibodies (MAbs) are preferred. In one embodiment of the invention, the MAbs are directed against a tumor-associated antigen in humans. Many monoclonal antibodies directed against specific target sites (e.g., cancer cells) in vivo have been developed. Examples of such MAbs are anti-TAC, or other interleukin-2 receptor antibodies; 9.2.27 and NR-ML-05 to a 250 kilodalton human melanoma associated proteoglycan; NR-LU-10 to 37–40 kilodalton pancarcinoma glycoprotein; and OVB$_3$ to an as yet unidentified cancer-associated antigen.

Known methods such as those of Kohler and Milstein (*Eur. J. Immunol.*, 6:292 (1976)) may be used to generate additional monoclonal antibodies reactive with a desired antigen. Monoclonal antibodies to tumor-associated antigens have been produced by several methods. One method is described in U.S. Pat. No. 4,172,124 and another different method is described in co-pending U.S. patent application Ser. No. 773,340, entitled "A Method for Improving the Elicitation of IgG Class Monoclonal Antibodies to Tumor-Associated Antigens and Glycoproteins".

The patterns of cross-reactivity for MAbs directed against a particular target site are analyzed to identify a set of two or more target-specific MAbs with non-overlapping cross-reactivity which may be used for a given diagnostic or therapeutic purpose. The antibodies produced may be screened by several methods. Advantageously, the in vitro testing procedure used to determine reactivity with tumors and cross-reactivity with normal tissues is immunohistochemical analysis. By immunohistochemical methods, the tissues (both normal and tumor tissues) to which the antibody in question binds are identified by exposing the tissue to the antibody and then detecting the presence of the antibody after washing to remove unbound antibody. Cryostat sections (i.e. frozen tissue sections produced as described in Example I below) are preferred since fixation may destroy particular antigens and is associated with uncertain differences in timing of fixation that may result in varying degrees of antigen preservation. Nonetheless, if a particular antigen is known to be preserved by fixation, then fixed tissues may also be used in the in vitro testing procedure.

Procedures for conducting in vitro immunohistochemical analyses are known. See, for example, Ceriani et al., *Cancer Research*, 47:532–540, Jan. 15, 1987. Another suitable in vitro assay is presented in Example I below. Thus, the normal tissue cross-reactivity of antibodies that are reactive with the desired target site may be evaluated in such assays, and two or more suitable antibodies are chosen for use as functionally specific antibodies.

The term "functionally specific antibodies" as used herein refers to two or more different antibodies which react with different epitopes on a particular target site, and have non-overlapping patterns of cross-reactivity with normal tissues. The use of two or more functionally specific antibodies in diagnostic or therapeutic procedures results in increased specificity toward target tissues compared to diagnostic or therapeutic agents comprising only one antibody or antibodies having similar patterns of cross-reactivity toward normal tissues, as described above.

Functionally specific antibodies react with the same tumor(s), but they need not react with all of the same cells in those tumors. For example, if two antibodies reacted with a separate population of tumor cells within the same tumor they could additively deliver radiation to that tumor. Functionally specific antibodies, however, will more commonly bind to overlapping populations of tumor cells.

Functionally specific antibodies must, however, not bind to all the same normal tissues. The less overlap there is in binding to normal tissues, the more functionally specific the antibody pairs. Any lack of overlap improves the tumor specificity compared to a single antibody alone, but a completely functionally specific antibody pair preferably will have no overlap or will overlap only on a nonessential organ or cell type. Examples of functionally specific antibodies include the monoclonal antibodies designated NR-LU-10 (also referred to as TFS-2) and NR-LU-11 (also referred to as TFS-4) that both react with small cell lung cancer, but both only cross react with thyroid although each alone reacts with several other normal tissues, as described in Example I below. Another example is NR-ML-05 and anti-GD3 antibodies that both react with melanoma, but both cross-react with no known normal tissue in common although each alone exhibits cross-reactivity with several normal tissues.

In one embodiment of the invention, the same diagnostic agent is attached to each of the different antibody species. Any suitable known diagnostic agent may be employed, including but not limited to radioisotopes such as $^{99m}Tc$, $^{111}In$, $^{123}I$, $^{131}I$, $^{76}Br$, or $^{18}F$, nuclear magnetic resonance imaging contrast agents, and the like. The radionuclides generally will be in the form of a stable complex, e.g., a chelate. The biodistribution of such diagnostic agents in vivo may be analyzed by appropriate standard external (i.e., non-invasive) means. A preferred diagnostic agent is the radionuclide metal $^{99m}Tc$. Following administration of a $^{99m}Tc$-labeled antibody, the biodistribution of the radionuclide metal may be detected by scanning the patient with a gamma camera using known procedures. Accumulations of $^{99m}Tc$ diagnostic agent at target sites are thus easily imaged.

In another embodiment of the invention, each antibody species has the same or a different therapeutic agent attached thereto. Any suitable known therapeutic agent may be used, including but not limited to therapeutically effective radionuclides, drugs, toxins, and biological response modifiers. The choice of agent will depend on the type of disease to be treated (i.e., the type of target cells). Such radioisotopes include, among others, $^{188}Re$, $^{186}Re$, $^{203}Pb$, $^{212}Pb$, $^{212}Bi$, $^{109}Pd$, $^{64}Cu$, $^{67}Cu$, $^{131}I$, $^{211}At$, $^{97}Ru$, $^{105}Rh$, $^{198}Au$, and $^{199}Ag$. The radionuclides generally are in the form of stable complexes such as chelates, which may be prepared by known methods.

Examples of toxins which may be employed are ricin, abrin, diphtheria toxin, Pseudomonas exotoxin A, ribosomal inactivating proteins, and mycotoxins; e.g., trichothecenes. Trichothecenes are a species of mycotoxins produced by soil fungi of the class fungi imperfecti or isolated from Baccharus megapotamica (Bamburg, J. R., *Proc. Molec. Subcell Bio.* 8:41–110, 1983; Jarvis & Mazzola, *Acc. Chem. Res.* 15:338–395, 1982). Therapeutically effective modified toxins or fragments thereof, such as those produced through genetic engineering or protein engineering techniques, may be used.

Any suitable therapeutic drug may be employed, depending on the nature of the patient's illness Among the many therapeutic drugs that have been used to treat various forms of cancer are nitrogen mustards such as L-phenylalanine nitrogen mustard and cyclophosphamide, intercalating agents such as cis diamino dichloro platinum, antimetabolites such as 5-fluorouracil, vinca alkaloids such as vincristine, and antibiotics such as adriamycin and bleomycin.

Drugs known to enhance the cytotoxic effect of certain anti-cancer drugs and radiotherapeutic agents also may be used. Such drugs are commonly referred to as sensitizers. The sensitizing drug may be attached to one antibody species and a radionuclide or appropriate anti-cancer drug attached to another antibody species, for example.

Among the sensitizers known to enhance the therapeutic effectiveness of radiation are metronidazole, misonidazole, certain 2-sulfamyl-6-nitrobenzoic acid derivatives, 2,6-disubstituted derivatives of 3-nitropyrazine, and certain isoindoledione compounds. (See U.S. Pat. Nos. 4,647,588; 4,654,369; 4,609,659; and 4,494,547.) Examples of sensitizers which enhance the activity of various therapeutic drugs (e.g., anti-cancer drugs) are buthionine sulfoximine, calcium channel blockers such as verapamil, and diltiazem. (See U.S. Pat. No. 4,628,047 and *Important Advances in Oncology* 1986, DeVita et al., Eds., J. B. Lippincott Co., Philadelphia, pages 146–157 (1986). One skilled in the art to which this invention relates will be able to identify appropriate combinations of sensitizers and therapeutic agents Examples of biological response modifiers are interferons (alpha, beta, and gamma), tumor necrosis factor, lymphotoxin, and interleukins (IL-1, -2, -3, -4, -5, and -6).

The procedure for attaching an agent to an antibody will vary according to the chemical structure of the agent. Antibodies are proteins which contain a variety of functional groups; e.g., carboxylic acid (COOH) or free amine ($-NH_2$) groups, which are available for reaction with a suitable functional group on an agent molecule to bind the agent thereto. Alternatively, the antibody and/or agent may be derivatized to expose or attach additional reactive functional groups. The derivatization may involve attachment of any of a number of linker molecules such as those available from Pierce Chemical Company, Rockford, Illinois. (See the Pierce 1986–87 General Catalog, pages 313–354.) A bifunctional linker having one functional group reactive with a group on a particular agent, and another group reactive with an antibody, may be used to form the desired immunoconjugate. Alternatively, derivatization may involve chemical treatment of the antibody; e.g., glycol cleavage of the sugar moiety of the glycoprotein antibody with periodate to generate free aldehyde groups. The free aldehyde groups on the antibody may be reacted with free amine or hydrazine groups on an agent to bind the agent thereto. (See U.S. Pat. No. 4,671,958.) Procedures for generation of free sulfhydryl groups on antibodies or antibody fragments also are known. (See U.S. Pat. No. 4,659,839.) Many procedures nd linker molecules for attachment of various compounds including radionuclide metal chelates, toxins and drugs to proteins such as antibodies are known. See, for example, European Patent Application Publication No. 188,256; U.S. Pat. Nos. 4,671,958; 4,659,839, 4,414,148; 4,699,784; 4,680,338; 4,569,789; and 4,590,071; and Borlinghaus et al. (*Cancer Research*, 47:4071–4075, Aug. 1, 1987).

A problem associated with some methods of linking certain therapeutic compounds to antibodies is that the biological activity of the compound (e.g., drug, toxin, etc.) may be reduced when the compound is attached to the antibody. When a therapeutic agent is conjugated to the antibody through a stable covalent bond, for example, release of the agent in its free, maximally active form at the target site generally would not be expected to occur. Therefore, immunoconjugates comprising linkages which are cleavable in the vicinity of the target site may be used when the desired activity of the agent would be diminished if not released from the antibody. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g., when exposed to tumor-associated enzymes or acidic pH) may be used.

A number of different cleavable linkers have been described previously. See U.S. Pat. Nos. 4,618,492; 4,542,225; and 4,625,014. The mechanisms for release of an agent from these linker groups include by irradiation of a photolabile bond, and acid-catalyzed hydrolysis. U.S. patent application Ser. No. 127,656 filed Dec. 2, 1987, entitled "Cleavable Immunoconjugates for the Delivery and Release of Agents in Native Form," discloses immunoconjugates comprising linkers of specified chemical structure, wherein the linkage is cleaved in vivo, releasing the compound (radiotherapeutic agent, drug, toxin, etc.) in its native form. The linker is susceptible to cleavage at mildly acidic pH, and is believed to be cleaved during transport into the cytoplasm of a target cell, thereby releasing the biologically active compound inside a target cell. U.S. Pat. No. 4,671,958 includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies, one skilled in the art will be able to determine a suitable method for attaching a given agent to an antibody.

The antibody-agent conjugates prepared as described above are administered to a human or mammalian host in diagnostically or therapeutically effective amounts. The amounts will vary depending on such factors as the antibodies used, since antibodies vary with respect to the number of receptors on the target cells and their affinity for the receptors. The dosage also will vary according to the agent used, as toxins and drugs, for example, vary with respect to their potency. It will be evident to one skilled in the art how to determine the optimal effective dose for a particular immunoconjugate. Procedures for determining the maximum tolerated dose for therapeutic agents, e.g., cytotoxic agents, also are known. Of course, since two or more different antibody species are used to deliver agents in vivo, the total dosage administered is the sum of the agents on all the different antibody species administered to the patient.

For many treatment methods currently in use, toxicity caused by the action of a therapeutic agent on normal tissues has been a dosage-limiting factor. Thus, dosages which would be more effective in eradication of target cells (e.g., cancer cells) could not be safely given due to the side effects caused by this toxicity. One of the advantages of the method of the present invention is that additive accumulation of therapeutic agent(s) on target cells occurs without additive accumulation of the agent(s) on cross-reactive normal tissues, due to the non-overlapping cross-reactivities. Thus, the total dosage administered may be increased to improve therapeutic effectiveness without increasing the undesirable side effects. The present invention thus provides an improved method for treatment of illness such as cancer when compared with other methods that employ a single antibody or a mixture of antibodies having overlapping cross-reactivities.

In diagnostic procedures, improved results may be achieved without increasing the dosage above conventional dosages. For example, target sites may be more accurately and effectively imaged due to the greater contrast between target and non-target tissues because of the non-additive binding of a diagnostic agent to non-target sites. Second, some metastases may express one antigen more than another. This provides the ability to target different metastases preferentially. Sequential administration of diagnostic imaging agents allows confirmation of sites of accumulation as true positives.

In therapeutic procedures, two or more antibody species, each having a different therapeutic agent attached thereto, may each be administered to a patient at the maximum tolerated dose, since each normal tissue type will bind only one of the immunoconjugates and therefore will not be exposed to the additive effects of both agents.

In another embodiment of the present invention, the antibodies may be covalently joined. One method is to link the Fab' fragment of one antibody species to the Fab or Fab' of the other. The hybrid F(ab')$_2$ would have bivalent binding to the target site but only univalent binding to any cross-reactive antigen. After administration of the hybrid antibody conjugated to a diagnostic or therapeutic substance, unconjugated native bivalent antibody could be used to displace the hybrid antibody from normal tissues where it has only univalent binding potential, and therefore lower affinity.

The present invention also provides a kit for diagnostic or therapeutic use comprising two or more antibody species wherein each of the antibody species is reactive with a different epitope on a target site and the patterns of cross-reactivity for each of said antibody species are non-overlapping. Thus, a particular kit contains functionally specific antibodies reactive with a desired target site such as a particular cancer site. The antibody species in a kit will vary according to the desired target site; e.g., whether the target cells are melanoma cells, SCLC cells, etc. Depending on the intended use of the antibodies, diagnostic or therapeutic agents may be attached to the antibodies, as described above. The antibodies in the kits may already have the agents attached thereto. Alternatively, the user (e.g., medical personnel) may attach the desired agent(s) to the antibodies before use.

In one embodiment of the invention, each antibody species in the kit has a chelating compound attached thereto. The chelating compound is capable of chelation of a diagnostically or therapeutically effective radionuclide metal. One kit of the present invention comprises two monoclonal antibody species designated NR-LU-10 and NR-LU-11, or fragments thereof, which bind to cancer cells.

The following examples are provided for purposes of illustration, not limitation.

EXAMPLE I. Two Antibodies Against Small Cell Lung Cancer

Three antibodies (KS 1/4,TFS-2 and TFS-4) that react with small cell lung cancer were recently described. See Varki, N. M., Reisfeld, R. A., and Walker, L. E., "Antigens Associated with a Human Lung Adenocarcinoma Defined By Monoclonal Antibodies." *Cancer Res* 44:681–87 (1984); Okabe T., Kaizu T., Fujisawa M. et al. "Monoclonal Antibodies to Surface Antigens of Small Cell Carcinoma of the Lung" *Cancer Res* 44:5273–78 (1984). Extensive evaluation on normal tissues by immunohistochemistry reveals that TFS-2 and KS 1/4 exhibit cross-reactive binding to normal thyroid, pancreas, hepatic ducts, and epithelial tissues, while TFS-4 binds to normal nerve tissues, adrenal glands, a subpopulation of circulating lymphocytes and thyroid gland. Both bind strongly and additively to small cell lung cancer cell lines. The in vitro testing procedure is as follows.

In summary, the assay comprises reacting murine monoclonal antibodies with antigens expressed on different cell type surfaces. Rabbit-anti-mouse antibodies conjugated to horseradish peroxidase then react with the murine antibodies. The peroxidase enzyme reduces hydrogen peroxide to water in the presence of 3,3'-diaminobenzidine (DAB), and a positive reaction product is indicated by a brown stain on the tissue. Monoclonal antibodies which are not of murine origin may be used in the test procedure provided that an appropriate secondary antibody conjugated to horseradish peroxidase is available for use.

One fact to be noted is that some tissues exhibit endogenous peroxidase staining. One tissue slide should be stained with DAB only to serve as a control for endogenous staining. A hematoxylin/eosin (H/E) stained section aids in the identification of different cell types. Appropriate negative control proteins are run with each set of serial sections tested with antibodies.

The slides are kept level during the entire staining procedure. Reagents should cover the entire tissue section and should not pool at either end of the slide. Slides which are not level and reagents which pool in one area of the tissue during staining will give inaccurate results. Specific time periods are assigned to each step of the staining procedure. Attention should be directed to timing of each staining step. Care should be taken not to scrape tissue during staining. Frozen sections may be fragile and should be handled gently and with care.

The reagent 3,3'-diaminobenzidine (DAB) maybe prepared in advance. DAB is available in 5.0 gram quantities. The DAB preparation should be done under a laminar flow hood while wearing single use medical gloves. To 5.0 grams DAB 20.0 ml HPLC grade water is added, and the DAB is dissolved. 200 ul of the DAB solution is transferred into each glass bottle until all of the solution has been used, and the bottles are placed in freezer boxes. The uncapped bottles are covered with several layers of utility wipers. The DAB solution is lyophilized in bottles for 2 days. The bottles then are removed from the lyophilizer, capped and frozen at $-70°$ C. until ready for use.

Reconstitution of lyophilized DAB is accomplished by removing 1 vial of DAB from $-70°$ C. freezer and allowing it to warm to room temperature on bench top. The assay for each monoclonal antibody then is conducted as follows:

In hood: add 5.0 ml phosphate buffered saline pH 7.0 without calcium/magnesium (PBS) to vial via needle and syringe. Pump solution up and down through syringe until DAB has dissolved. Filter entire DAB solution through a 0.45 micron filter into 95 ml PBS. DAB should be made fresh with every immunoperoxidase test and should not be reconstituted more than 30 minutes prior to use. 0.03% $H_2O_2$ activates the DAB.

Filter approximately 15 ml of chicken serum through a 115 ml 0.45 micron filter. The chicken serum must be filtered daily for use in frozen section staining. Make a 5% solution of chicken serum in PBS (PBS-CS). Make appropriate dilutions of test antibodies (5 ug/ml is an appropriate dilution for most test and control antibodies). Also prepare rabbit and anti-mouse (RaM) conjugate 1/50 in PBS-CS plus 4% human serum type AB. Spin solutions in an ultracentrifuge for 1 hour at 100,000 x g at 4° C. Note that RaM conjugate must be spun daily. Conjugate not used in making the 1/50 working dilution should be discarded. Do not save. It is not always necessary for primary test antibodies to be spun (e.g., supernatants may be used as is). The test antibodies are contacted with samples of various normal human tissues which have been fixed onto glass slides previously. The procedure for preparation of the fresh frozen tissue specimens bound to slides is as follows, using a variable temperature cryochamber and microtome (available from Cryostat):

1. Frozen tissue/OCT mold is affixed to cutting chuck with liquid OCT which quickly freezes at $-20°$ C.
2. Mount chuck to cryo-microtome chuck holder.
3. Orient chuck for proper sectioning.
4. Tissue is sectioned at 4–6 microns.
5. Sections are mounted to dry glass microslides (which have been previously subbed with an aqueous 5% gelatin solution and allowed to dry.
6. Glass microslides with tissue sections are then fixed in cold acetone (precooled to $-20°$ C.) for 10 minutes.
7. Fixed tissue slides are then placed in a 37° C. incubator to thoroughly evaporate the acetone.

If not used immediately, the tissue-bearing slides may be prepared for storage as follows:

1. Place (dry) acetone fixed slides in plastic microslide holder; replace lid.
2. Wrap box with aluminum foil.
3. Put foil wrapped box in plastic zip-lock bag with 2–3 desicant packets - seal shut with minimal air space.
4. Store in $-70°$ C. freezer.
5. Prior to use, allow acetone fixed slides to reach room temperature. Slides should be completely dry. Rehydrate slides in PBS for 10 minutes.
6. The test antibodies are contacted with the tissue-bearing slides as follows:

Incubate slides for 20 minutes with 100 ul PBS with 5% chicken serum (PBS-CS) containing 4% pooled normal rabbit serum to block non-specific binding. Rinse slides with PBS using 500ml squirt bottle. Incubate sections with 100 ul test antibody (undilute or at appropriate dilution) to assess antigen expression or with 100ul PBS-CS only to visualize endogenous murine immunoglobulin. Rinse slides with PBS. Agitate in two fresh PBS washes in large beakers for 5 and 10 minutes respectively. Incubate each slide with 100 ul rabbit-anti-mouse immunoglobulin conjugated to horseradish peroxidase (RaM-HRPO) diluted 1/50 in PBS-CS plus 4% human serum for 30 minutes. Rinse sections with PBS and agitate in three fresh 5-minute PBS washes.

Incubate slides collectively in DAB 0.5 mg/ml with 0.03% hydrogen peroxide for 10 minutes. Rinse in PBS bath. Counterstain slides for 1 to 1-½ minutes with Mayer hematoxylin. Rinse in PBS bath. Dip slides in a saturated lithium carbonate aqueous solution used for bluing. Rinse in PBS bath. Dehydrate sections with 5 minute incubations in 30%, 60%, 75% 200° ethanol, 200° ethanol, and xylene respectively. Mount sections with a small amount of Permount and a #1 micro coverglass. Slides may be stored for observation under the microscope or saved for further reference.

As previously described, a positive reaction is indicated by a brown reaction product. A negative reaction slide will appear to be blue. Slides are scored for percent of cells stained, intensity of the stain, and homogeneity of the stain. The types of tissue with which a particular antibody reacts are thereby identified.

The above-described patterns of cross reactivity for the three antibodies were thereby determined. A different procedure was used to test reactivity of these antibodies toward small cell lung cancer (SCLC) cell lines designated SHITE-1. TSF-4 and KS-14 react with different antigens. Each reacts with small cell lung cancer.

The antibodies were incubated at 4° C. for 1 hour with the cells, washed and then goat anti-mouse FITC was added to the test. The results are presented in FIG. 1. The shaded areas represent the number of cells (Y-axis) with a given fluorescence intensity (X-axis) as determined by flow cytometry. KS-14 and TSF-2 exhibit identical profiles, so KS-14 was used for "addition" experiments TSF-4 demonstrated a unique profile, but when added to KS-14, there was clear additive binding as shown by the large number of cells accumulating in the highest fluorescence channel. When $P_3$, a control antibody that is not reactive with SCLC was added, no such "synergy" occurred.

The above in vitro testing procedures demonstrate that antibody TSF-4 together with either TSF-2 or KS-¼ may be used as functionally specific antibodies in accordance with the present invention.

EXAMPLE II. Immunoconjugates from Two Antibodies Against Small Cell Lung Cancer The two antibody species TFS-2 and TFS-4 each are covalently linked to the anti-cancer drug doxorubicin through a suitable linker molecule. The linker molecule 5 and procedure described in U.S. Pat. No. 4,680,388 may be used. The resulting immunoconjugates are separately tested for the maximum tolerated dose (MTD) to humans. This is achieved by administering single or multiple fixed doses to groups of patients (usually 3–5), monitoring for toxicity and determining the MTD as the dose level below which limiting toxicity was reached. Doxorubicin itself commonly causes reversible bone marrow depression, alopecia, mucositis and irreversible cardiomyopathy at cumulative doses in excess of 550 mg/m². When linked to an antibody for delivery to tumor and possibly normal cross-reactive tissues, its toxicities would be expected to be different, and dependent on cross-reactivity. TFS-4, for example, when linked to doxorubicin may cause neurotoxicity at some dose and TFS-2 doxorubicin may result in thyroid or pancreatic toxicity. Dosages may be modified accordingly. Both immunoconjugates are administered near their MTD to a patient with SCLC. Both immunoconjugates are expected to accumulate additively on the tumor cells, without overlapping toxicity toward essential normal tissues.

EXAMPLE III. Potentiation of Cytotoxicity Using Immunoconjugates of Two Antibodies Against Small Cell Lung Cancer Buthionine sulfoximine (BSO) is a synthetic amino acid that inhibits gamma-glutamylcysteine synthetase and leads to a marked reduction in glutathione (GHS) in cells. BSO has been reported to enhance the effectiveness of certain anti-cancer drugs. BSO is synthesized or is obtained from Chemical Dynamics Corporation, South Plainfield, New Jersey. The BSO is linked to monoclonal antibody TFS-4.

A synthetic scheme for conjugating BSO to antibody is as follows:

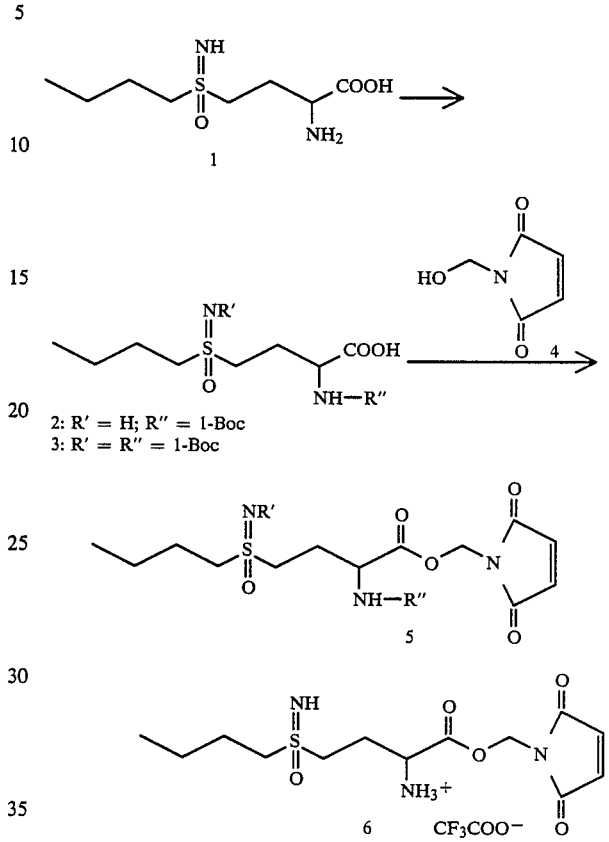

2: R' = H; R" = 1-Boc
3: R' = R" = 1-Boc

Preparation of N,N'-Bis(t-butoxycarbonyl)buthionine sulfoximine 3: To a stirred solution of buthionine sulfoximine (1.6 g, 5 mmol) in THF-H₂O (1:1, 25 mL) was added Et₃N (750 uL, 1.1 equiv) followed by di-tert-butylpyrocarbonate (4.5 g, 4.1 equiv). The clear biphasic mixture was stirred for 15 h. At the end tetrahydrofuran was evaporated in vacuo and MeOH (15 mL), Et₃N (750 μL) were added and to the homogeneous solution were added portions of di-tert-butylpyrocarbonate (15.25 g, 14 equiv, 2 equiv/48 h during the first 96 h and then 5 equiv/48 h during the later 96 h) over a period of 8 days. Reversed phase TLC, MeOH-H₂O (7:3) showed mainly two spots (RF=0.7 and 0.4) after spraying and heating with ninhydrin. Acetic acid (1 mL) was added to the reaction mixture and volatiles were evaporated in vacuo and the residue reevaporated with toluene in vacuo. The resulting oil was dissolved in MeOH and water was added to slight turbidity. It was then charged onto a $C_{18}$ column equilibrated with MeOH-H₂O (3:7) and eluted with MeOH-H₂O (3:7, 500 mL), MeOH-H₂O (2:3, 250 mL), MeOH-H₂O (1:1, 200 mL), MeOH-H₂O (3:1, 300 mL) and finally with MeOH (300 mL) collecting fractions of 75 mL size. Fractions containing N-t-butoxycarbonylbuthionine sulfoximine 2 were combined and evaporated in vacuo to give 1.05 g as a powder. 1H NMR'H (CDCl₃) δ8.1 (2H, exchangeable with D₂O, br's), 5.8 (1H, exchangeable with D₂O, br.s), 4.3 (1H, m), 3.2 (4H, m), 2.3 (2H, m), 2.0–0.8 (16 H, m). Fractions containing N,N'-bis(t-butoxycarbonyl)buthionine sulfoximine 3 were combined and evaporated in vacuo to give 450 mg as a foam. ¹H NMR (CDCl₃)δ6.0–5.5 (2H, exchangeable with D₂O, br's), 4.40 (1H, m), 3.4 (4H, m), 2.5–2.2 (2H, m), 1.8 (2H, m), 1.48, 1.45 (18 H, 2xS), 0.97 (3H, t, J=7Hz). ¹³C NMR (CDCl₃)δ176.3, 158.9, 156.4, 80.8, 80.3, 51.5 51.3, 48.1, 48.0, 28.3, 28.1, 27.9, 25.5, 24.3, 24.1, 21.5, 13.5.

Preparation of N,N'-Bis(t-butoxycarbonyl)sulfoximine (maleimido)methyl ester 5: A solution of 3 (290 mg, 0.7 mmol) in CH₂Cl₂ (3 mL) under argon was cooled to 0° C. and Et₃N (100 μL) was added. After 10 min. isobutyl chloroformate (120 μL) was added dropwise via a syringe. The solution was stored at 0° C. under argon for 1 h. A solution of N-hydroxymethylmaleimide 4 (89 mg, 0.7 mmol) in CH₂Cl₂ (2 mL) then was added dropwise and the amber colored suspension was stirred at 0° C. for 30 min at which time TLC, silica gel, MeOH-CH₂Cl₂ (1:19) indicated completion of the reaction. The reaction mixture was diluted with CH₂Cl₂ (15 mL) and partitioned between water (10 mL) and CH₂Cl₂. Organic layer was dried (Na₂SO₄), filtered, evaporated in vacuo. The residue (370 mg) was subjected to flash chromatography with MeOH-CH₂Cl₂ (1:19) on 1×15 cm silica gel column. Fractions containing N,N'-bis(tbutoxycarbonyl)buthionine sulfoximine (maleimido)methyl ester 5 were combined and evaporated in vacuo to give a pale yellow oil (230 mg, 62%). ¹H NMR (CDCl₃)δ6.8, (2H, S), 5.6 (24, m), 5.2 (1H, m), 4.3 (1H, m), 3.5–3.1 (4H, m), 1.5–2.1 (2H, m), 1.8 (2H, m), 1.48, 1.45 (18H, 2S), 0.95 (3H, t, J=7.0 H2).

Preparation of Sulfoximine (maleimido) methyl ester 6: A solution of 5 (71 mg) in CH₂Cl₂ (350 uL) was treated with anhydrous TFA (50 uL). Pale yellow solution was stored at ambient temperature overnight. TLC, silica gel, MeOH-CHCl₃ (1:9) and n-BuOH-AcOH-H₂O (3:2:1) indicated completion of the reaction. Volatiles were evaporated. The crude product was triturated with Et₂O (2×5 mL) and washings discarded. ¹H NMR (D₂O) of the residue showed δ 6.8 (2H, S), 5.6 (2H, m), 4.6 (1H, m, partly buried under H₂O peak), 3.6–3.2 (4H, m), 2.4–2.2 (2H, m), 1.8–1.5 (2H, m), 1.4–1.2 (2H, m), 0.8 (3H, t, J=7.0 Hz) which is consistent with the proposed structure.

The BSO derivative 6 is conjugated to the monoclonal antibody TFS-4 (described above). The maleimide group of the BSO derivative is reacted with a free sulfhydryl on the antibody to form the immunoconjugate. The reaction procedures are generally as described in U.S. Pat. No. 4,659,839. Preferably, the reaction procedure begins with isolation of a Fab' fragment from the antibody. This may be accomplished by conventional procedures; e.g., by first treating the antibody with papain to generate a F(ab')₂ fragment (see Parham et al., *J. Immunol. Methods*, 53:133–173 [1982]). The F(ab')₂ fragment is treated with a reducing agent such as dithiothreitol, 2-mercaptoethanol, or cysteine under mild reducing conditions to preferentially cleave the single disulfide bond between the two heavy chains without breaking the disulfide bonds between heavy and light chains. The two resulting Fab' fragments each have one free sulfhydryl group. These Fab' fragments are reacted with the derivatized BSO compound in a suitably buffered solution under conditions which will not damage the antibody fragment. Suitable buffers include such nontoxic buffers as sodium phosphate buffer, phosphate buffered saline, and sodium bicarbonate buffers, advantageously at a concentration of about 1.0 M and a pH near about 7.0. The resulting immunoconjugate is represented by the following formula in which Ab represents the antibody fragment:

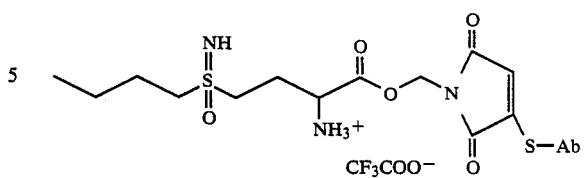

Doxorubicin is covalently linked to TFS-2 as described in Example II. The TFS-4/BSO is administered to an SCLC patient at its maximum tolerated dose, as is the TFS-2/ doxorubicin. Because BSO can potentiate adriamycin toxicity, and because only the tumor cells and thyroid receive both BSO and doxorubicin, the tumor cells should be more sensitive to the doxorubicin than any of the normal tissues except thyroid with which the TFS-2 antibody cross-reacts. Possible thyroid failure may be easily monitored by T₄, T₃ and TSH levels, and replacement hormone completely ameliorates the problems associated with hypothyroidism.

EXAMPLE IV. Immunoconjugates Comprising a Radiotherapeutic Compound

A chelate comprising the therapeutically effective radionuclide metal ¹⁸⁸Re and having the following structural formula is prepared:

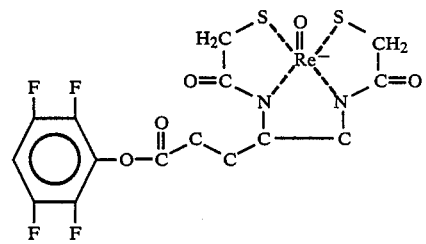

Preparation of this chelate is as described in European Patent Application Publication No. EP 188,256 or in co-pending U.S. patent application Ser. No. 065,011. Sodium perrhenate (3 mL, 15 mCi, produced from a W-188/ Re-188 research scale generator) was added to a vial containing a lyophilized mixture comprising citric acid, 75 mg; stannous chloride, 0.75 mg; gentisic acid, 0.25 mg; and lactose, 100 mg. The vial was agitated gently to mix the contents, then incubated at room temperature for 10 minutes to form a ¹⁸⁸Re-citrate exchange complex. Next, 0.50 mL of isopropyl alcohol was added to a separate vial containing 0.50 mg of 2,3,5,6-tetrafluorophenyl-4,5bis[S-(1-ethoxyethyl)thioace-tamido]pentanoate, which is a chelating compound comprising ethoxyethyl sulfur protective groups and a 2,3,5,6-tetrafluorophenyl ester group, having the formula:

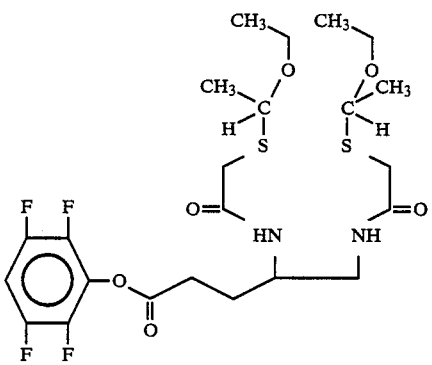

The vial was agitated for two minutes to completely dissolve the chelating compound. Next, 0.30 mL of this solution was transferred to the vial containing the $^{188}$Re-citrate complex prepared above. After gentle mixing, the vial was incubated in a 75° C. ±2° C. water bath for 15 minutes, then immediately transferred to a 0° C. ice bath for two minutes. The yields of $^{188}$Re-labeled chelate then ranged between 75% and 90% as measured by reversed phase $C_{18}$ HPLC analysis.

A column containing a $C_{18}$ reversed phase low-pressure material (Baker $C_{18}$ cartridges) was used to purify the $^{188}$Re-labeled chelate. After conditioning of the cartridge with ethanol and water, the sample was loaded and washed with three times 2 mL of water and three times 2 mL of 20% ethanol/0.01 M phosphate buffer. The column was then dried in vacuo and eluted with two times 1.0 mL acetonitrile. About 75% of the $^{188}$Re-radioactivity was recovered in greater than 95% purity as the ester chelate compound. The organic solvent was then evaporated under a flow of inert gas.

The chelate is then conjugated to a Fab fragment of monoclonal antibody TFS-2 and a Fab fragment of TFS-4 in separate reaction mixtures. The Fab fragments are generated by papain treatment according to conventional procedures.

A buffered solution of the antibody fragment (5 mg/mL, 0.5 mL) is added to the purified $^{188}$Re-labeled chelate, followed by 0.5 mL of 0.5 M carbonate/bicarbonate buffer pH 9.50. The reaction is kept at room temperature for 15 minutes, then 25 mg of L-lysine, 0.1 mL, is added and the reaction is pursued at room temperature for 15 minutes more.

A column containing Sephadex G-25 material is used to purify each $^{188}$Re-labeled immunoconjugate. The reaction mixture is loaded on top of the column, and 1.2 mL aliquots are collected using PBS buffer to rinse the reaction vial and elute the $^{188}$Re immunoconjugate in the third and fourth fractions.

The immunoconjugate is then further diluted with PBS, and radioactivity is measured prior to injection of both immunoconjugates into an SCLC patient. The two immunoconjugates should accumulate additively only on SCLC and thyroid tissues within the patient, and the additive therapeutic dosage of both immunoconjugates is selectively directed to the target tissue.

Current data suggests that doses of B-emitting radionuclides linked to antibodies will be limited by their effects on the bone marrow. One approach to overcome this problem is to harvest and store the marrow prior to treatment. The second target organ of toxicity will then be related to the cross-reactivity of the antibody and the molecular species (whole antibody, F(ab')$_2$, Fab or Fv) used. Doses up to 400 mCi $^{131}$I on whole ant body have been safely administered when marrow is harvested and stored for re-infusion.

Radiosensitizers such as misonidazole and BSO (see Example III) may be used to potentiate the cytotoxicity of radionuclides on tumors just as they can drugs. If suitable potentiation occurs, the radiation dose administered may be decreased and bone marrow spared. Radionuclides would be coupled to one antibody and the sensitizer would be coupled to the other antibody in the pair.

EXAMPLE V. Immunoconjugates Comprising a Radiodiagnostic Compound

The chelating compound shown in Example IV may be radiolabeled with the metal radionuclide $^{99m}$Tc, a diagnostic agent, as described in EP 188,256 or U.S.Ser. No. 065,011.

One mL of sterile water for injection was added to a sterile vial containing a stannous gluconate complex (50 mg sodium gluconate and 1.2 mg stannous chloride dihydrate, available from Merck Frosst, Canada, in dry solid form) and the vial was gently agitated until the contents were dissolved. A sterile insulin syringe was used to inject 0.1 mL of the resulting stannous gluconate solution into an empty sterile vial. Sodium pertechnetate (0.75 mL, 75–100 mCi, eluted from a $^{99}$Mo/$^{99}$Tc generator purchased from duPont, Mediphysics, Mallinckrodt or E. R. Squibb) was added, and the vial was agitated gently to mix the contents then incubated at room temperature for 10 minutes to form a $^{99m}$Tc-gluconate complex.

A separate vial containing 0.3 mg of the chelating agent in dry solid form was prepared by dispensing a solution of 0.3 mg chelating agent in acetonitrile into the vial, then removing the solvent under $N_2$ gas. To this vial was then added 0.87 mL of 100% isopropyl alcohol, and the vial was gently shaken for about two minutes to completely dissolve the chelating agent, which was 2,3,5,6tetrafluorophenyl 4,5-bis[S-(1-ethoxyethyl)thioacetamido]pentanoate. Next, 0.58 mL of this solution of the chelating agent was transferred to a vial containing 0.16 mL of glacial acetic acid /0.2 N HCl (2:14), and the vial was gently agitated. Of this acidified solution, 0.5 mL was transferred to the vial containing the 99mTc-gluconate complex, prepared above. After gentle agitation to mix, the vial was incubated in a 75° C. ±2° C. water bath for 15 minutes, then immediately transferred to a 0° C. ice bath for two minutes.

To a separate vial containing 10 mg of the Fab fragment of a monoclonal antibody (TSF-2 or TSF-4 as described in Example IV) in 0.5 mL of phosphate buffered saline, is added 0.37 mL of 1.0 M sodium bicarbonate buffer, pH 10.0. The vial is gently agitated.

The vial containing the acidified solution of the $^{99m}$Tc-labeled chelate (see above) is removed from the ice bath, 0.1 mL of the sodium bicarbonate buffer is added, and the vial is agitated to mix. Immediately, the buffered antibody solution (above) is added, gently agitated to mix and incubated at room temperature for 20 minutes to allow conjugation of the radiolabeled chelate to the antibody.

A column containing an anion exchanger, either DEAE-Sephadex or QAE-Sephadex, is used to purify each of the two immunoconjugates. The column is prepared under aseptic conditions as follows. Five 1 mL QAE-Sephadex columns are connected to form a single column. Alternatively, a single 5 mL QAE-Sephadex column may be used. The column is washed with 5 mL of 37 mM sodium phosphate buffer, pH 6.8. A 1.2 u filter (available from Millipore) is attached to the column, and a 0.2 u filter is attached to the 1.2 u filter. A 22-gauge sterile, nonpyrogenic needle is attached to the 0.2 u filter.

The reaction mixture is drawn up into a 3 mL or 5 mL syringe, and any air bubbles are removed from the solution. After removal of the needle, the syringe is connected to the QAE-Sephadex column on the end opposite the filters. The needle cap is removed from the 22-gauge needle attached to the filter end of the column and the needle tip is inserted into a sterile, nonpyrogenic test tube. Slowly, over two minutes, the reaction mixture is injected into the column. The eluant collected in the test tube is discarded. The now empty syringe on top of the column is replaced with a 5 mL syringe containing 5 ml of 75 mM (0.45%) sodium chloride solution (from which air bubbles have been removed.) The needle at the other end of the column is inserted aseptically into a sterile, nonpyrogenic 10 mL serum vial. Slowly, over two minutes, the NaCl solution is injected into the column, and the eluent is collected in the serum vial.

A total radioactivity in the serum vial is measured using a dose calibrator. The contents of both serum vials are combined and drawn up into a sterile, pyrogen-free, 30 cc syringe and diluted to a total volume of 30 mL with sterile 0.9% NaCl for injection of each immunoconjugates into a human SCLC patient sequentially over a few days. The two radiodiagnostic agent-bearing antibodies should accumulate additively on the target cancer tissue and on thyroid tissue.

One major benefit of using the two radiodiagnostic agents, compared to a single antibody, is to detect metastases expressing only one of the antigens in sufficient abundance to accumulate the antibody. With negligible overlapping cross-reactivity on normal tissues, the two antibodies may also distinguish real foci of tumor (both tests are positive) from normal tissue accumulation (only 1 test positive). The known uptake of the tracer into highly vascularized areas, or into kidneys if Fab fragments are employed, needs to be considered in this evaluation.

I claim:

1. A method of delivering one or more diagnostic or therapeutic agents to a target site within a mammalian or human host, comprising administering to said host two or more different antibody species each having one of said agents attached thereto, wherein each of said antibody species is reactive with a different epitope of the target site and wherein the patterns of cross-reactivity for each antibody species are non-overlapping.

2. The method of claim 1 wherein the target site is a cancer site.

3. The method of claims 1, 2 wherein one antibody species is monoclonal antibody NR-LU-10 or a fragment thereof, and a second antibody species is NR-LU-11 or a fragment thereof.

4. The method of claim 1 wherein an identical therapeutic agent is attached to each of the antibody species.

5. The method of claim 4 wherein the therapeutic agent is $^{188}$Re in the form of a chelate.

6. The method of claim 1 wherein each of the antibody species is a monoclonal antibody or a fragment thereof.

7. The method of claim 6 wherein each antibody species is a monoclonal antibody, or a fragment thereof, which binds to cancer cells.

8. The method of claim 1 wherein an identical diagnostic agent is attached to each of the antibody species.

9. The method of claim 8 wherein the diagnostic agent is a diagnostically effective radionuclide.

10. The method of claim 9 wherein the diagnostic agent is selected from the group consisting of $^{99m}$Tc, $^{131}$I, $^{111}$In, and $^{123}$I, $^{76}$Br, and $^{18}$F.

11. The method of claim 10 wherein the diagnostic agent is $^{99m}$Tc in the form of a chelate.

12. The method of claim 1 wherein different therapeutic agents are attached to each of the antibody species.

13. The method of claim 12 wherein the target site is a cancer site, a sensitizing drug is attached to one antibody species, and a therapeutically effective radionuclide is attached to a second antibody species.

14. The method of claim 12 wherein the target site is a cancer site, a sensitizing drug is attached to one antibody species, and an anti-cancer drug is attached to a second antibody species.

15. The method of claim 14 wherein the sensitizing drug is buthionine sulfoximine and the anti-cancer drug is doxorubicin.

16. The method of claim 1, 4, or 12 wherein each therapeutic agent is selected from the group consisting of therapeutically effective radionuclides, drugs, toxins, sensitizers, and biological response modifiers.

17. The method of claim 16 wherein the radionuclide is selected from the group consisting of $^{188}$Re, $^{186}$Re, $^{203}$Pb, $^{212}$Pb, $^{212}$Bi, $^{109}$Pd, $^{64}$Cu, $^{67}$Cu, $^{131}$I, $^{211}$At, $^{97}$Ru, $^{105}$Rh, $^{198}$Au, and $^{199}$Ag.

18. The method of claim 16 wherein the toxin is selected from the group consisting of ricin, abrin, diphtheria toxin, Pseudomonas exotoxin A, ribosomal inactivating proteins, mycotoxins, trichothecenes, and therapeutically effective fragments thereof.

19. The method of claim 16 wherein said target site is a cancer site and the drug is an anti-cancer drug.

20. The method of claim 19 wherein the drug is an anti-cancer antibiotic.

21. The method of claim 20 wherein the drug is doxorubicin.

22. A method of producing additive accumulation of two or more immunoconjugates on a target tissue within a human or mammalian host while minimizing additive accumulation of the immunoconjugates on non-target tissues, comprising:
   a) administering a first immunoconjugate comprising a first antibody species to the host;
   administering one or more additional immunoconjugates each comprising a different antibody species to the host, wherein each of the antibody species reacts with a different epitope of the target tissue and the different antibody species have non-overlapping patterns of cross-reactivity wherein each of said first and additional immunoconjugates comprise a therapeutic or diagnostic agent attached to an antibody species.

23. The method of claim 22 wherein each immunoconjugate comprises a diagnostic agent attached to an antibody species.

24. The method of claim 23 wherein the diagnostic agent is a diagnostically effective radionuclide.

25. The method of claim 24 wherein the diagnostic agent is selected from the group consisting of $^{99m}$Tc, $^{131}$I, $^{111}$In, $^{123}$I, $^{76}$Br, and $^{18}$F.

26. The method of claim 22, 23 wherein the target tissue comprises cancer cells.

27. The method of claim 26 wherein each antibody species is a monoclonal antibody, or a fragment thereof, which binds to the cancer cells.

28. The method of claim 27 wherein one antibody species is monoclonal antibody NR-LU-10 or a fragment thereof, and a second antibody species is NR-LU-11 or a fragment thereof.

29. The method of claim 22 wherein each immunoconjugate comprises a therapeutic agent attached to an antibody species.

30. The method of claim 29 wherein different therapeutic agents are attached to each of the antibody species.

31. The method of claim 29 or 30 wherein each therapeutic agent is selected from the group consisting of therapeutically effective radionuclides, drugs, sensitizers, toxins, and biological response modifiers.

32. The method of claim 31 wherein each radionuclide is selected from the group consisting of $^{188}$Re, $^{186}$Re, $^{203}$Pb, $^{212}$Pb, $^{212}$Bi, $^{109}$Pd, $^{64}$Cu, $^{131}$I, $^{211}$At, $^{97}$Ru, $^{105}$Rh, $^{198}$Au, and $^{199}$Ag.

33. The method of claim 31 wherein each toxin is selected from the group consisting of ricin, abrin, diphtheria toxin, Pseudomonas exotoxin A, ribosomal inactivating proteins, mycotoxins, trichothecenes, and therapeutically effective fragments thereof.

34. The method of claim 31 wherein said target tissue comprises cancer cells and each drug is an anti-cancer drug.

35. The method of claim 31 wherein the target tissue comprises cancer cells, a sensitizer is attached to one antibody species, and a therapeutically effective radionuclide or anti-cancer drug is attached to a second antibody species.

36. A method of administering two or more different therapeutic agents to a human or mammalian host to eradicate target cells, wherein each therapeutic agent is administered at its maximum tolerated dose to the host, while minimizing toxicity toward non-target tissues, comprising attaching each different therapeutic agent to a different antibody species, wherein each, antibody species, reacts with a different epitope of the target cells, and wherein the patterns of cross-reactivity for each antibody species are non-overlapping, and administering each of the resulting immunoconjugates at the maximum tolerated dose to the host.

37. The method of claim 36 wherein each therapeutic agent is selected from the group consisting of therapeutically effective radionuclides, drugs, toxins, and biological response modifiers.

38. The method of claim 36 wherein the target cells are cancer cells.

39. The method of claim 38 wherein each of the antibody species is a monoclonal antibody, or a fragment thereof, which binds to the cancer cells.

40. The method of claim 29 wherein one antibody species is monoclonal antibody NR-LU-10 or a fragment thereof, and a second antibody species is NR-LU-11 or a fragment thereof.

* * * * *

UNITED STATES PATENT AND TRADEMARK OFFICE
CERTIFICATE OF CORRECTION

PATENT NO. : 4,867,962
DATED : September 19, 1989
INVENTOR(S) : Paul G. Abrams

It is certified that error appears in the above-identified patent and that said Letters Patent is hereby corrected as shown below:

In claim 22, column 18, line 50, before "administering" insert --b)--.

In claim 36, column 20, line 12, after "wherein each" please delete --,--; and on line 13, after "species" please delete --,--.

In claim 40, column 20, line 27, please delete "29" and insert --39--.

Signed and Sealed this

Twenty-second Day of December, 1992

Attest:

DOUGLAS B. COMER

*Attesting Officer*   *Acting Commissioner of Patents and Trademarks*

UNITED STATES PATENT AND TRADEMARK OFFICE
CERTIFICATE OF CORRECTION

PATENT NO. : 4,867,962
DATED : September 19, 1989
INVENTOR(S) : Paul G. Abrams

It is certified that error appears in the above-indentified patent and that said Letters Patent is hereby corrected as shown below:

column 5, line 39, please delete "$^{199}$Ag" and insert -- $^{199}$Au --.

In claim 3, column 17, line 55, please delete "1, 2" and insert -- 1, 4, 5, 7, 8, 11, 12 or 15 --.

In claim 17, column 18, line 31, please delete "$^{199}$Ag" and insert -- $^{199}$Au --.

In claim 26, column 18, line 67, after "23", please insert -- or 29 --.

In claim 32, column 19, line 22, please delete "$^{199}$Ag" and insert -- $^{199}$Au --.

Signed and Sealed this

Eighteenth Day of June, 1996

Attest:

BRUCE LEHMAN

*Attesting Officer*     *Commissioner of Patents and Trademarks*